United States Patent [19]

Weissman

[11] 4,375,965
[45] Mar. 8, 1983

[54] DENTAL IMPRESSION TRAY ASSEMBLY

[75] Inventor: Bernard Weissman, New York, N.Y.

[73] Assignee: IPCO Corporation, White Plains, N.Y.

[21] Appl. No.: 273,663

[22] Filed: Jun. 15, 1981

[51] Int. Cl.³ .............................................. A61C 9/00
[52] U.S. Cl. ..................................................... 433/37
[58] Field of Search ........................ 433/37, 38, 39, 45

[56] References Cited
FOREIGN PATENT DOCUMENTS
210868  6/1909  Fed. Rep. of Germany ........ 433/37

Primary Examiner—Robert Peshock
Attorney, Agent, or Firm—Goodman & Teitelbaum

[57] ABSTRACT

A dental impression forming apparatus including a dental impression tray in which a negative impression of a dental area is to be formed in dental impression material. Apertures are provided in the tray for passage of dental impression material therethrough. A cover member is supplied with the dental impression material, and is fitted over the tray. Upon application, in situ, of the cover member onto the tray, the dental impression material is forced through the apertures into the tray and around the dental area so that the negative impression can be formed. Preferably, guide pins are provided on the tray and corresponding holes are provided in the cover member to align the cover member with the tray, and guide the cover member toward the tray when a force is applied on the cover member.

12 Claims, 4 Drawing Figures

DENTAL IMPRESSION TRAY ASSEMBLY

BACKGROUND OF THE INVENTION

This invention relates to dental impression trays, and more particularly to a method and apparatus for forming negative impressions of dental areas in a patient's mouth.

In connection with performing restoration of defective dental areas, it is frequently necessary to form negative impressions of the dental area which is to be restored. In order to form such negative impressions, it is generally well known in the dental art to utilize a dental impression tray. Such trays are typically arcuately shaped in plan, and have a substantially U-shaped cross-sectional configuration so as to provide a trough for receiving dental impression material.

Typically, the trough of the dental impression tray is first filled with the dental impression material, and the filled impression tray is then seated on the dental area to be restored. Pressure is applied onto the dental impression tray so as to press the teeth into the dental impression material to form a negative impression within the material. The tray is generally held in the mouth until the impression material hardens and is then removed from the mouth. Subsequent steps are then carried out in accordance with conventional practices.

One problem with utilizing such dental impression trays is that much of the dental impression material will be forced out between the impression tray and the dental area, and form a flash about the dental area to be restored. Additionally, by pressing down directly onto the tray, a direct force is applied onto the dental area and frequently, where the dental area is weak, defective, or loose, breakage of the dental area is possible. Also, it is difficult to actually see the dental area when covered with the tray, and to determine whether a suitable negative impression has been made.

In order to alleviate some of these problems, apertures are formed in the dental impression tray, especially in the bottom wall of the tray. By means of such apertures, the flash is reduced since the excess dental impression material flows through the apertures and out of the tray itself. Although the use of the apertures alleviates some of the problems concerning the flash, it introduces new problems since inaccurate negative impressions might be achieved. When utilizing an apertured dental impression tray, as the force is being applied onto the tray so as to seat the tray on the dental area, a resisting force is being provided by the teeth into the impression material. This resisting force pushes the impression material through the apertures of the tray and away from the teeth. As a result, the dental impression material does not flow completely around the dental area and, as a result, portions of the dental area may not be completely surrounded by the dental impression material. For example, the space between adjacent teeth may not be completely filled with the impression material since both adjacent teeth will push the impression material through the tray apertures and, accordingly, suitable negative impressions may not be formed.

SUMMARY OF THE INVENTION

It is therefore an object of the present invention to provide a dental impression tray assembly which avoids the aforementioned problems of prior art devices.

Another object of the present invention is to provide a dental impression tray assembly which permits the formation of negative impressions with greater accuracy, greater ease, and more efficiency.

Still another object of the present invention is to provide a dental impression forming apparatus having a dental impression tray provided with a cover member acting in cooperation therewith to form more accurate negative impressions.

Yet another object of the present invention is to provide a dental impression forming apparatus including a dental impression tray provided with a cover member having a substantially similar configuration as the tray, and wherein the tray has apertures therein so that dental impression material placed in the cover member can be forced through the apertures into the tray.

An additional object of the present invention is to provide a method of forming a negative impression of a dental area which provides more accurate negative impressions using simpler operations in the mouth area.

Yet a further object of the present invention is to provide a dental impression tray of semi-rigid material having apertures therein, a pressure member of flexible material for covering the tray, the tray being provided with guide pins thereon which are received in corresponding holes in the pressure member to align the pressure member with the tray as the pressure member is being forced toward the tray so that the dental impression material in the pressure member is forced through the apertures into the tray to thereby provide more accurate negative impressions.

Briefly, in accordance with the present invention there is provided a dental impression forming apparatus including a dental impression tray of semi-rigid material in which a negative impression of the dental area is to be formed in dental impression material. Apertures are formed in the tray for passage therethrough of the dental impression material. A cover member of flexible material is included which fits over the tray. The cover member receives the dental impression material and upon application, in situ, of the cover member onto the tray, the dental impression material is forced through the apertures and into the tray, so that the impression material fits around the dental area and a negative impression of the dental area is formed in the impression material.

The tray has a substantially trough-shape configuration for fitting over the dental area, the apertures being formed in the base wall. The cover member covers the apertures for application of a force thereon so as to force the dental impression material into the tray and around the dental areas. The tray is provided with guide pins which are received in corresponding holes in the cover member to align the cover member with the tray as the cover member is being forced toward the tray. Additional apertures are provided in the side walls of the tray for added retention of the impression material in the tray once the negative impression is formed so that the negative impression can be removed from the dental area.

The invention also contemplates a method of forming a negative impression of a dental area. A dental impression material is first placed in a trough area of an arcuately-shaped cover member, and the cover member is positioned on a correspondingly shaped dental impression tray having apertures therein. The tray and cover member are then seated onto the dental area. Preferably, some dental impression material is also placed in the tray. The cover member is then pushed onto the tray so as to force the impression material from the cover member through the apertures and into the tray so as to surround the dental area with impression material to form the negative impression.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which.

In the various figures of the drawing, like reference characters designate like parts.

DESCRIPTION OF THE PREFERRED EMBODIMENTS

Figure 1:
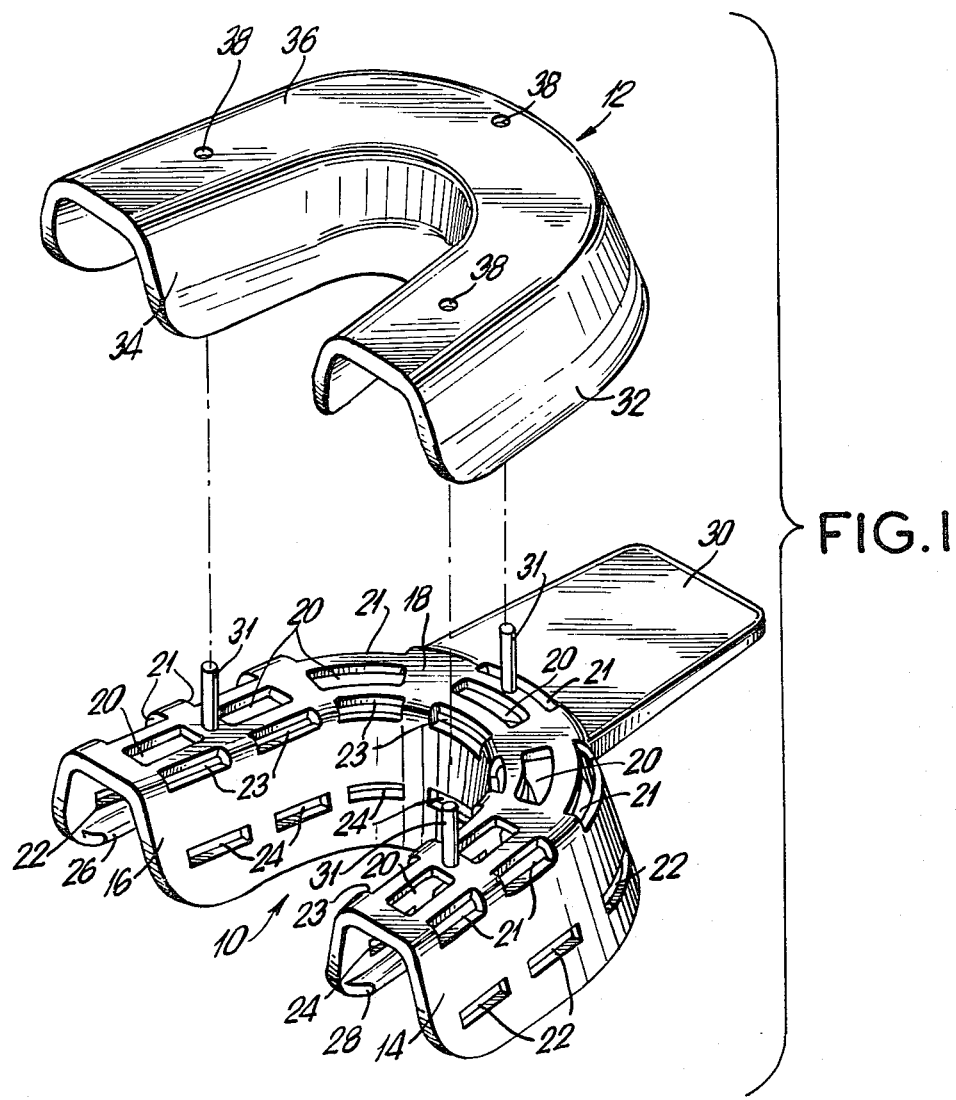
FIG. 1 is an exploded perspective view of the dental impression forming apparatus of the present invention.

Referring now to FIG. 1, the dental impression forming apparatus of the present invention is shown to include a dental impression tray, shown generally at 10, and a cover or pressure member, shown generally at 12. The dental impression tray 10 has a substantially arcuately shaped planar configuration. As shown, it is U-shaped or a semi-ellipse which can fit over the entire lower or upper set of teeth. However, other arcuate sections can be utilized, such as a half-tray or other similar section so as to fit only a portion of the lower or upper set of teeth. Other well known configurations could be also utilized.

In cross-sectional configuration, the tray is substantially U-shaped having an outer leg 14 connected to an inner leg 16 by an interconnecting base wall 18 to provide a trough. Elongated slots 20 are formed in the base wall. The slots are longitudinally spaced apart and fit peripherally along the base wall. In addition, slots 21 are formed between the interconnection of the outer leg 14 and the base wall 18, and slots 22 are formed in the lower portion of leg 14. Similarly, slots 23 are formed at the interconnection between the inner leg 16 and the base wall 18, and slots 24 are formed in the lower portion of leg 16. It should be understood that other aperture configurations could be used.

The lower edges of the outer and inner legs 14 and 15 are inwardly directed to form retaining lips 26, 28. A rearwardly extended handle 30 extends from the outer leg 14 so as to facilitate grasping of the tray. Guide pins 31 extend upwardly from the base wall 18, there preferably being one pin 31 on each leg portion of the U-shaped base wall 18 and the third pin 31 on the light portion thereof.

The cover member 12 has a shape substantially conforming to that of the tray 10. Specifically, it also is arcuately shaped in planar configuration, and as shown, it forms a U-shape or a semi-ellipse. However, if other sized or shaped arcuate sections of the tray would be utilized, as indicated above, correspondingly sized and shaped sections of the cover member would be provided.

The cover member 12 is also U-shaped in cross-sectional configuration, including an outer wall 32 connected to an inner wall 34 by an interconnecting base wall 36 to provide a trough. It should be noted, that the cover member 12 is substantially solid and does not include any of the above-mentioned apertures therein. The shape of the cover member is such that its side walls 32, 34 form a sliding interference fit with the side walls 14, 16 of the tray 10, so that the cover member walls 14, 16 are forced outwardly and spread apart when placing the cover member 12 onto the tray 10. Accordingly, the side walls 32, 34 are tapered downwardly from the base wall 36 to provide thinner side walls which are more flexible so that the side walls 32, 34 can be easily spread apart. Furthermore, the free end portions of the side walls 32, 34 have an increased taper to further decrease the thickness thereof for even more flexibility of the free end portions.

Holes 38 are provided through the base wall 36 of the cover member 12, there preferably being one hole 38 in each leg portion of the U-shaped base wall 36 and the third hole 38 in the light portion thereof corresponding to the location of the guide pins 31 of the tray 10. The holes 38 are sized to receive the associated guide pins 31 therein so that the cover member 12 can be aligned with the tray 10. Accordingly, the guide pins 31 function to guide the cover member 12 down onto the tray 10 as the cover member 12 is being forced or pushed toward the tray 10, as set forth below.

Utilization of the dental impression forming apparatus shown in FIG. 1 will now be described in connection with FIGS. 2–4. Initially, the cover member 12 is filled with the impression material 40. Such impression material 40 is well known in the dental art and any of various types of impression material can be utilized.

Figure 2:
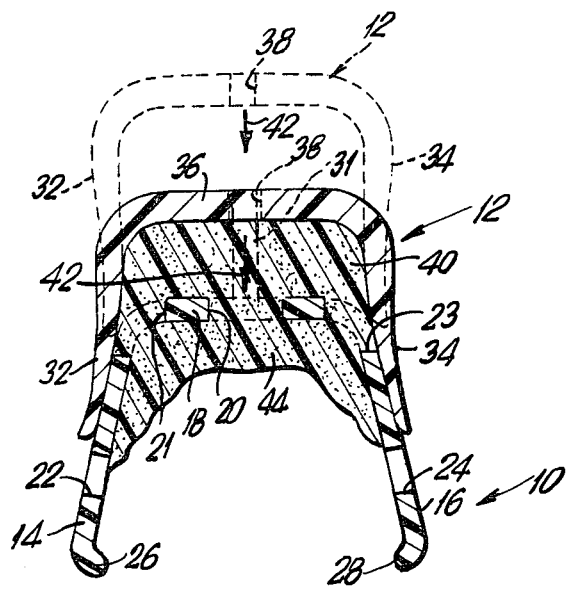
FIG. 2 is a cross-sectional elevational view showing the initial application of the cover member onto the tray, the cover member being positioned so as to force the dental impression material into the tray.

After the cover member 12 is supplied with the impression material 40, it is placed over the tray 10 and is pushed downwardly in the direction shown by the arrows 42 until the guide pins 31 extend into the corresponding holes 38 to align the cover member 12 and the tray 10, as shown in FIG. 2. At this point some of the dental impression material 40 flows through the apertures 20, 21 and 23. Preferably, additional impression material 44 is now placed in the tray 10 against the base wall 18.

It should be noted that initially, the cover member side walls 32, 34, as shown in dotted lines, are spaced close together when first placed onto the tray 10. Upon application of a force to push the cover member 12 onto the tray 10, the side walls 34, 36 move outwardly and spread apart so as to fit over the side walls 14, 16 of the tray. Accordingly, the inherent flexibility and resiliency of the walls 32, 34 will permit such spreading apart, and provide a tight fit between the cover member 12 and the tray 10.

Figure 3:
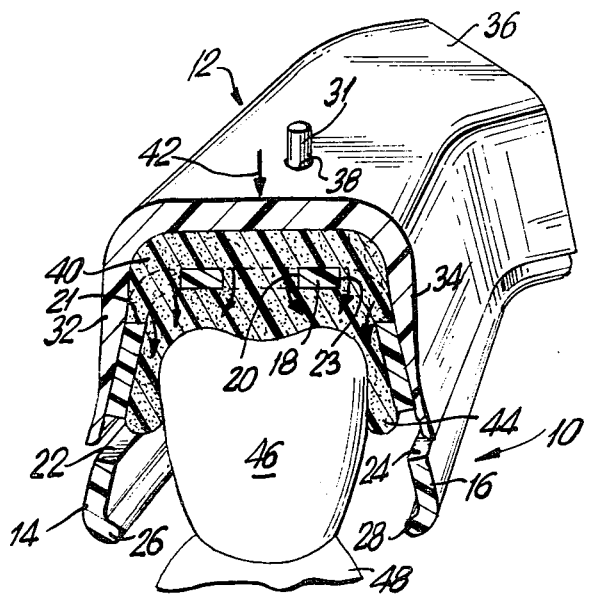
FIG. 3 is a cross-sectional perspective view showing the seating of the tray and cover member onto a dental area with the impression material being forced into the tray and around the dental area.

After the cover member and tray are coupled together by the guide pins 31 and by means of the dental impression material 40, the tray 10 with the cover member 12 thereon is then seated onto the dental area, as shown in FIG. 3. Specifically, it is placed over a tooth 46 with the impression material 44 fitting onto the tooth. The cover member 12 is then pushed further down onto the tray member 10, being guided by the guide pins 31 which extend through the holes 38, so that the dental impression material 40 continuously flows downward through the apertures 20, 21, 23, as shown by the arrows in FIG. 3. As the dental impression material 40, 44 flows downward into the tray, it is forced completely around the tooth 46, such that sections of the dental impression material flow downward toward the gum 48 and start to fill the apertures 22, 24 in the side walls 14, 16 of the tray 10.

Figure 4:
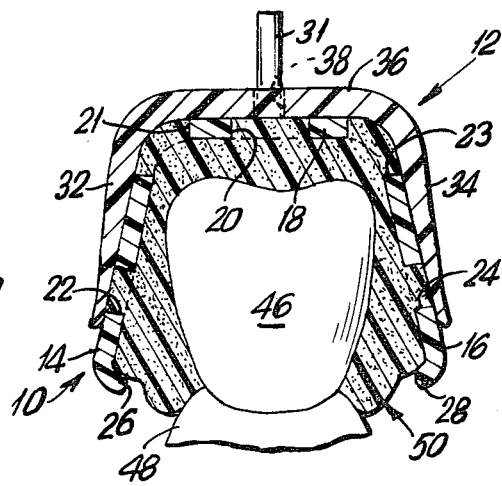
FIG. 4 shows a cross-sectional elevational view of the cover member being seated securely onto the tray with the dental impression material fitting around the dental area, whereby a negative impression can be formed in the dental impression material.

As shown in FIG. 4 with the cover member 12 completely fitting over the tray 10, the dental impression material 40, 44, will surround the tooth 46 and extend downward onto the gum 48 so as to form a complete covering about the dental area. The dental area forms a negative impression within the impression material 40, 44 which hardens to form a negative mold 50. Upon removal of the tray, the negative impression of the negative mold 50 can then be further utilized to form a positive mold, in accordance with standard dental technology. It is noted, that portions of the negative mold 50 are disposed in the apertures 22, 24 of the tray 10 which provide additional retention to aid in the removal of the negative mold from the dental area, whereby the negative mold is secured to the tray 10. Obviously, the portions of the negative mold 50 in the apertures 20, 21 and 23 provide the main retention of the negative mold in the tray 10.

It should be appreciated, that without the use of the cover member, if the tray would be forced downward onto the dental area, the tooth would normally resist against the dental impression material forcing it outwardly through the apertures. As a result, the impression material would not completely surround the tooth area. By means of application of a force onto the cover member, however, a counterforce is provided against the resistance of the tooth so as to retain the dental material within the tray and force it completely around all parts of the tooth area so that an accurate negative impression can be formed.

The materials of the tray and cover are typically formed of plastic so as to keep the cost of such devices at a minimum, to facilitate sterilization, and also to provide the necessary inherent flexibility and resiliency needed for the cover member to fit onto the tray member. However, other materials could be used. Preferably, the tray is formed from a semirigid plastic material and the cover member is formed from a flexible plastic material.

By means of the present apparatus, it is easier for the dentist to view the area in which the negative impression is to be formed and facilitate his utilization of the device so as to permit better negative impressions to be formed.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A dental impression forming apparatus comprising:
   a dental impression tray in which a negative impression of a dental area is to be formed in dental impression material;
   aperture means provided in said tray for passage therethrough of the dental impression material into said tray;
   cover means for forcing the dental impression material through said aperture means into said tray;
   said cover means including a cover member fitting over said tray for receiving the dental impression material therein, whereby upon application, in situ, of said cover member onto said tray, the dental impression material is forced through said aperture means into said tray and around the dental area;
   said tray and said cover member being provided with alignment means to guide said cover member toward said tray; and
   said alignment means including at least one guide pin disposed on said tray and a corresponding cooperating hole provided in said cover member for receiving said guide pin therethrough.

2. A dental impression forming apparatus as in claim 1, wherein said cover member has a configuration substantially conforming to configuration of said tray.

3. A dental impression forming apparatus as in claim 2, wherein said tray has an arcuate configuration in plan, and has a substantially U-shaped cross-sectional configuration to provide side walls and an interconnecting base wall, and wherein said aperture means includes apertures provided at least in said base wall.

4. A dental impression forming apparatus as in claim 3, wherein said cover member has a substantially U-shaped cross-sectional configuration to provide side walls and an interconnecting base wall, and wherein said cover member and said tray member provide a sliding interference fit such that said side walls of said cover member spread apart to fit over said side walls of said tray.

5. A dental impression forming apparatus comprising:
   a dental impression tray in which a negative impression of a dental area is to be formed in dental impression material;
   aperture means provided in said tray for passage therethrough of the dental impression material into said tray;
   cover means for forcing the dental impression material through said aperture means into said tray;
   said cover means including a cover member fitting over said tray for receiving the dental impression material therein, whereby upon application, in situ, of said cover member onto said tray, the dental impression material is forced through said aperture means into said tray and around the dental area;
   said cover member having a configuration substantially conforming to configuration of said tray;
   said tray having an arcuate configuration in plan, and having a substantially U-shaped cross-sectional configuration to provide side walls and an interconnecting base wall;
   said aperture means including apertures provided at least in said base wall of said tray;
   said cover member having a substantially U-shaped cross-sectional configuration to provide side walls and an interconnecting base wall;
   said cover member and said tray member providing a sliding interference fit such that said side walls of said cover member spread apart to fit over said side walls of said tray; and
   said side walls of said cover member being decreasingly tapered from said cover member base wall to provide a thinner cross-section than said cover member base wall so that said cover member side walls are flexible.

6. A dental impression forming apparatus comprising:

a dental impression tray in which a negative impression of a dental area is to be formed in dental impression material;

aperture means provided in said tray for passage therethrough of the dental impression material into said tray;

cover means for forcing the dental impression material through said aperture means into said tray;

said cover means including a cover member fitting over said tray for receiving the dental impression material therein, whereby upon application, in situ, of said cover member onto said tray, the dental impression material is forced through said aperture means into said tray and around the dental area;

said tray having an arcuate configuration in plan, and having a substantially U-shaped cross-sectional configuration to provide side walls and an interconnecting base wall;

said cover member having a substantially U-shaped cross-sectional configuration to provide side walls and an interconnecting base wall;

said cover member having a configuration substantially conforming to configuration of said tray so that said cover member and said tray member provide a sliding fit such that said side walls of said cover member fit over said side walls of said tray, and said base wall of said cover member is engageable with said base wall of said tray; and said tray and said cover member being provided with alignment means to guide said base wall of said cover member towards and into engagement with said base wall of said tray as said side walls of said cover member slide over said side walls of said tray, so that the dental impression material is forced into said tray.

7. A dental impression forming apparatus as in claim 6, wherein said aperture means includes apertures provided at least in said base wall of said tray.

8. A dental impression forming apparatus as in claims 3, 5 or 7, wherein said apertures are also provided at an interconnection between said tray side walls and said tray base wall.

9. A dental impression forming apparatus as in claims 3, 5 or 6, and further comprising inwardly directed retaining lips provided at distal ends of said tray side walls.

10. A method of forming a negative impression of a dental area, comprising:
 (a) placing dental impression material into a trough area of an arcuately-shaped cover member;
 (b) placing the cover member on a correspondingly shaped dental impression tray having apertures therein, and seating the tray onto the dental area; and
 (c) pushing the cover member toward the tray so as to force the impression material from the cover member, through the apertures, and into the tray, so as to surround the dental area with impression material.

11. A method as in claim 10, and further comprising the step of placing the cover member onto the tray and pushing some of the impression material into the tray through the apertures prior to seating onto the dental area.

12. A method as in claim 10, and further comprising the step of placing additional impression material in the tray prior to seating onto the dental area.

* * * * *